US008357656B2

(12) United States Patent
Simari et al.

(10) Patent No.: US 8,357,656 B2
(45) Date of Patent: Jan. 22, 2013

(54) NATRIURETIC PEPTIDE RECEPTOR-C AGONISTS

(75) Inventors: Robert D. Simari, Rochester, MN (US); Shuchong Pan, Rochester, MN (US); John C. Burnett, Jr., Rochester, MN (US); Horng H. Chen, Rochester, MN (US); Lincoln R. Potter, Roseville, MN (US)

(73) Assignees: Mayo Foundation for Medical Education and Research, Rochester, MN (US); Regents of the University of Minnesota, Saint Paul, MN (US)

( * ) Notice: Subject to any disclaimer, the term of this patent is extended or adjusted under 35 U.S.C. 154(b) by 86 days.

(21) Appl. No.: 12/677,838

(22) PCT Filed: Sep. 15, 2008

(86) PCT No.: PCT/US2008/076434
§ 371 (c)(1),
(2), (4) Date: Aug. 23, 2010

(87) PCT Pub. No.: WO2009/036448
PCT Pub. Date: Mar. 19, 2009

(65) Prior Publication Data
US 2010/0311660 A1 Dec. 9, 2010

Related U.S. Application Data

(60) Provisional application No. 60/972,778, filed on Sep. 15, 2007.

(51) Int. Cl.
*A61P 13/12* (2006.01)
*C07K 14/435* (2006.01)
(52) U.S. Cl. ........................... 514/15.4; 530/324
(58) Field of Classification Search .................. None
See application file for complete search history.

(56) References Cited

U.S. PATENT DOCUMENTS

| 4,034,074 | A | 7/1977 | Miles |
|---|---|---|---|
| 4,098,876 | A | 7/1978 | Piasio et al. |
| 4,233,402 | A | 11/1980 | Maggio et al. |
| 4,496,544 | A | 1/1985 | Needleman |
| 4,996,143 | A | 2/1991 | Heller et al. |
| 5,114,923 | A | 5/1992 | Seilhamer et al. |
| 5,212,286 | A | 5/1993 | Lewicki et al. |
| 5,296,347 | A | 3/1994 | LaMotte, III |
| 5,434,133 | A | 7/1995 | Tanaka et al. |
| 5,565,322 | A | 10/1996 | Heller |
| 5,580,859 | A | 12/1996 | Felgner et al. |
| 5,583,108 | A | 12/1996 | Wei et al. |
| 5,589,466 | A | 12/1996 | Felgner et al. |
| 5,665,704 | A | 9/1997 | Lowe et al. |
| 5,674,710 | A | 10/1997 | Seilhamer et al. |
| 5,846,932 | A | 12/1998 | Lowe et al. |
| 5,849,489 | A | 12/1998 | Heller |
| 5,948,761 | A | 9/1999 | Seilhamer et al. |
| 6,124,430 | A | 9/2000 | Mischak et al. |
| 6,162,603 | A | 12/2000 | Heller |
| 6,376,207 | B1 | 4/2002 | Mischak et al. |
| 6,551,795 | B1 | 4/2003 | Rubenfield et al. |
| 6,586,396 | B1 | 7/2003 | Seilhamer et al. |
| 6,812,339 | B1 | 11/2004 | Venter et al. |
| 6,818,619 | B2 | 11/2004 | Burnett, Jr. et al. |
| 6,828,107 | B2 | 12/2004 | Asada et al. |
| 6,849,714 | B1 | 2/2005 | Bridon et al. |
| 6,887,470 | B1 | 5/2005 | Bridon et al. |
| 6,887,481 | B1 | 5/2005 | Chan et al. |
| 6,897,030 | B2 | 5/2005 | Seilhamer et al. |
| 6,974,861 | B2 | 12/2005 | Seilhamer et al. |
| 7,179,790 | B2 | 2/2007 | Seilhamer et al. |
| 7,214,786 | B2 | 5/2007 | Kovalic et al. |
| 7,332,569 | B2 | 2/2008 | Cojocaru et al. |
| 2004/0123343 | A1 | 6/2004 | Rosa et al. |
| 2007/0281887 | A1 | 12/2007 | Pan |

FOREIGN PATENT DOCUMENTS

| WO | WO84/03285 | 10/1984 |
|---|---|---|
| WO | WO95/24419 | 9/1995 |
| WO | WO00/71576 | 11/2000 |
| WO | WO01/44284 | 6/2001 |
| WO | WO02/24895 | 3/2002 |
| WO | 2005/000095 | 1/2005 |
| WO | 2005/072055 | 8/2005 |

OTHER PUBLICATIONS

Sabbatini et al., Atrial natriuretic factor stimulates exocrine pancreatic secretion in the rat through NPR-C receptors, Am. J. Physiol. Gastrointest. Liver Physiol. 285, G929-G937, 2003.*
Abbey and Potter, "Vasopressin-dependent Inhibition of the C-type Natriuretic Peptide Receptor, NPR-B/GC-B, Requires Elevated Intracellular Calcium Concentrations," *J. Biol. Chem.*, 2002, 277:42423-42430.
Anand-Srivastava, "Natriuretic peptide receptor-C signaling and regulation," *Peptides*, 2005, 26:1044-1059.
International Preliminary Report on Patentability in PCT/US2008/076434, issued Mar. 16, 2010, 5 pages.
International Search Report and Written Opinion of the International Searching Authority in PCT/US2008/076434, mailed May 19, 2009, 6 pages.
Bryan and Potter, "The Atrial Natriuretic Peptide Receptor (NPR-A/GC-A) Is Dephosphorylated by Distinct Microcystin-sensitive and Magnesium-dependent Protein Phosphatases," *J. Biol. Chem.*, 2002, 277:16041-16047.
Chen et al., "A novel designer natriuretic and diuretic peptide based upon an alternatively spliced BNP without vascular vasodilatory actions," *Circulation*, 2006, 114(18): 270.
Fan et al., "Down-Regulation Does Not Mediate Natriuretic Peptide-Dependent Desensitization of Natriuretic Peptide Receptor (NPR)-A or NPR-B: Guanylyl Cyclase-Linked Natriuretic Peptide Receptors Do Not Internalize," *Mol. Pharmacol.*, 2005, 67:174-183.
Genbank Accession No. ADW08083, dated Mar. 24, 2005.
Genbank Accession No. AEB63460, dated Oct. 20, 2005.

(Continued)

*Primary Examiner* — Elly-Gerald Stoica
(74) *Attorney, Agent, or Firm* — Fish & Richardson P.C.

(57) ABSTRACT

This document relates to methods and materials involved in preferentially activating natriuretic peptide receptor-C polypeptides. For example, agonists of natriuretic peptide receptor-C polypeptides as well as methods for activating natriuretic peptide receptor-C polypeptides are provided herein.

2 Claims, 5 Drawing Sheets

OTHER PUBLICATIONS

Mathur et al., "Nesiritide—A new agent for acute decompensated heart failure," *Medical Journal of Armed Forces India*, 2005, 61(4):375-376.

Pan et al., "Biodesign of a renal-protective peptide based on alternative splicing of B-type natriuretic peptide," *PNAS*, 2009, 106(27):11282-11287.

Rose et al., "C-type natriuretic peptide activates a non-selective cation current in acutely isolated rat cardiac fibroblasts via natriuretic peptide C receptor-mediated signaling," *J. Physiol.*, 2007, 580(Pt. 1):255-274.

Sabbatini et al., "C-type natriuretic peptide stimulates pancreatic exocrine secretion in the rat: Role of vegal afferent and efferent pathways," *Eur. J. Pharmacol.*, 2007, 577:192-202.

Chen et al., "Equimolar doses of atrial and brain natriuretic peptides and urodilatin have differential renal actions in overt experimental heart failure," *Am. J. Physiol. Regul. Integr. Comp. Physiol.*, 2005, 288:R1093-R1097.

Chen et al., "Renal response to acute neutral endopeptidase inhibition in mild and severe experimental heart failure," *Circulation*, 1999, 100:2443-2448.

Cole et al., "The EBV-hybridoma technique and its application to human lung cancer," *Monoclonal Antibodies and Cancer Therapy*, 1985, Alan R. Liss, Inc., pp. 77-96.

Costello-Boerrigter et al., "Vasopressin-2-receptor antagonism augments water excretion without changes in renal hemodynamics or sodium and potassium excretion in human heart failure," *Am. J. Physiol. Renal Physiol.*, 2006, 290:F273-F278.

Cote et al., "Generation of human monoclonal antibodies reactive with cellular antigens," *Proc. Natl. Acad. Sci. USA*, 1983, 80:2026-2030.

Cowie and Mendez, "BNP and congestive heart failure," *Prog. Cardiovasc. Dis.*, 2002, 44(4):293-321.

GenBank Accession No. BQ130005 dated Jul. 15, 2003, 2 pages.

GenBank Accession No. BQ130258 dated Jul. 15, 2003, 2 pages.

GenBank Accession No. M25296 dated Apr. 27, 1993, 1 page.

Gevaert et al., "Protein identification based on matrix assisted laser desorption/ionization-post source decay-mass spectrometry," *Electrophoresis*, 2001, 22(9):1645-1651.

Guatelli et al., "Isothermal, in vitro amplification of nucleic acids by a multienzyme reaction modeled after retroviral replication," *Proc. Natl. Acad. Sci. USA*, 1990, 87:1874-1878.

Haber et al., "Application of a radioimmunoassay for angiotensin I to the physiologic measurements of plasma renin activity in normal human subjects," *J. Clin. Endocr.*, 1969, 29:1349-1355.

Huse et al., "Generation of a large combinatorial library of the immunoglobulin repertoire in phage lambda," *Science*, 1989, 246:1275-1281.

Hyrup and Nielsen, "Peptide nucleic acids (PNA): synthesis, properties and potential applications," *Bioorgan. Med. Chem.*, 1996, 4:5-23.

Köhler and Milstein, "Continuous cultures of fused cells secreting antibody of predefined specificity," *Nature*, 1975, 256:495-497.

Kozbor and Roder, "The production of monoclonal antibodies from human lymphocytes," *Immunology Today*, 1983, 4:72-79.

Lewis, "PCR's competitors are alive and well and moving rapidly towards commercialization," *Genetic Engineering News*, 1992, 12(9):1-3.

Margulies et al., "Induction and prevention of radiocontrast-induced nephropathy in dogs with heart failure," *Kidney International*, 1990, 38(6):1101-1108.

McCurley et al., "Furosemide and the progression of left ventricular dysfunction in experimental heart failure," *J. Am. Coll. Cardiol.*, 2004, 44(6):1301-1307.

Ogawa et al., "Molecular cloning of the complementary DNA and gene that encode mouse brain natriuretic peptide and generation of transgenic mice that overexpress the brain natriuretic peptide gene," *J. Clin. Invest.*, 1994, 93(5):1911-1921.

Pawson et al., "Assembly of cell regulatory systems through protein interaction domains," *Science*, 2003, 300:445-452.

Peacock, "The B-type natriuretic peptide assay: a rapid test for heart failure," *Cleve. Clin. J. Med.*, 2002, 69(3):243-251.

Richards et al., "BNP in hormone-guided treatment of heart failure," *Trends Endocrinol. Metab.*, 2002, (5):151-155.

Sackner-Bernstein et al., Risk of worsening renal function with nesiritide in patients with acutely decompensated heart failure, *Circulation*, 2005, 111:1487-1491.

Sagnella, "Practical implications of current natriuretic peptide research," *J. Renin. Angiotensin Aldosterone Syst.*, 2000, 1(4):304-315.

Summerton and Weller, "Morpholino antisense oligomers: design, preparation, and properties," *Antisense Nucleic Acid Drug Dev.*, 1997, 7:187-195.

Suzuki et al., "The role of the natriuretic peptides in the cardiovascular system," *Cardiovascular Res.*, 2001, 51:489-494.

Tremblay et al., "Biochemistry and physiology of the natruiretic peptide receptor guanylyl cyclases," *Mol. Cell. Biochem.*, 2002, 230(1-2):31-47.

Valli et al., "Review of 10 years of the clinical use of brain natriuretic peptide in cardiology," *J. Lab Clin. Med.*, 1999, 134(5):437-444.

Walther et al., "Natriuretic peptide system in fetal heart and circulation," *J. Hypertens.*, 2002, 20(5):786-791.

Wei et al., "Atrial and pulmonary endothelin mRNA is increased in a canine model of chronic low cardiac output," *Am. J. Physiol.*, 1997, 273:R838-844.

Weiss, "Hot prospect for new gene amplifier," *Science*, 1991, 254:1292-1293.

Non-Final Office Action in U.S. Appl. No. 10/561,014, mailed Sep. 5, 2008, 23 pages.

Final Office Action in U.S. Appl. No. 10/561,014, mailed Jun. 12, 2009, 18 pages.

Non-Final Office Action in U.S. Appl. No. 10/561,014, mailed Dec. 29, 2009, 13 pages.

Final Office Action in U.S. Appl. No. 10/561,014, mailed Jul. 21, 2010, 11 pages.

Non-Final Office Action in U.S. Appl. No. 10/561,014, mailed Oct. 12, 2011, 14 pages.

Office action in Chinese Application No. 200480020964.7, dated Aug. 9, 2010, 16 pages.

Office action in European Application No. 04754213.9, dated Jan. 20, 2009, 7 pages.

Office action in European Application No. 04754213.9, dated May 29, 2009, 6 pages.

Office action in Israel Application No. 172674, dated Apr. 5, 2009, 2 pages.

Office action in Israel Application No. 172674, dated Aug. 8, 2010, 2 pages.

Office action in Japanese Application No. 2006-517173, dated Feb. 16, 2010, 6 pages.

Office Action in Japanese Application No. 2009-523978, dated Jul. 25, 2012, 15 pages.

International Search Report in International Application No. PCT/US2007/075465, mailed Dec. 18, 2007, 15 pages.

International Preliminary Report on Patentability in International Application No. PCT/US2007/075465, mailed Feb. 19, 2009, 8 pages.

Supplementary European Search Report and Annex in European Application No. EP 07 81 3886, completed Jan. 11, 2010, 7 pages.

U.S. Office Action in U. S. Appl. No. 10/561,014, mailed Jun. 12, 2009, 18 pages.

Extended European Search Report in European Application No. 10187879.1, dated Mar. 9, 2011, 7 pages.

Abdelhafiz, "Heart failure in older people: causes, diagnosis and treatment," *Age Ageing*, 2002, 31(1):29-36.

Best et al., "Dendroaspis natriuretic peptide relaxes isolated human arteries and veins," *Cardiovas. Res.*, 2002, 55:375-384.

Bowie et al., "Deciphering the message in protein sequences: tolerance to amino acid substitutions," *Science*, 1990, 247:1306-1310.

Burger and Burger, "BNP in decompensated heart failure: Diagnostic, prognostic and therapeutic potential," *Curr. Opin. Investig. Drugs*, 2001, 2(7):929-35.

Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell Biol.*, 1990, 111:2129-2138.

Chaurand et al., "Peptide and protein identification by matrix-assisted laser desorption ionization (MALDI) and MALDI-post-source decay time-of-flight mass spectrometry," *J. Am. Soc. Mass. Spectrom.*, 1999, 10(2):91-103.

\* cited by examiner

SEQUENCE LISTING

```
<160> NUMBER OF SEQ ID NOS: 4

<210> SEQ ID NO 1
<211> LENGTH: 42
<212> TYPE: PRT
<213> ORGANISM: Artificial Sequence
<220> FEATURE:
<223> OTHER INFORMATION: synthetic polypeptide

<400> SEQUENCE: 1

Ser Pro Lys Met Val Gln Gly Ser Gly Cys Phe Gly Arg Lys Met Asp
 1               5                  10                  15

Arg Ile Ser Ser Ser Ser Gly Leu Gly Cys Lys Gly Lys His Pro Leu
            20                  25                  30

Pro Pro Arg Pro Pro Ser Pro Ile Pro Val
        35                  40

<210> SEQ ID NO 2
<211> LENGTH: 18
<212> TYPE: PRT
<213> ORGANISM: Artificial Sequence
<220> FEATURE:
<223> OTHER INFORMATION: synthetic polypeptide

<400> SEQUENCE: 2

Ala Asp Thr Val Arg Val Thr Leu Gly Phe Val Val Ser Gly Asn His
 1               5                  10                  15
```

```
Thr Leu

<210> SEQ ID NO 3
<211> LENGTH: 60
<212> TYPE: PRT
<213> ORGANISM: Artificial Sequence
<220> FEATURE:
<223> OTHER INFORMATION: synthetic polypeptide

<400> SEQUENCE: 3

Ser Pro Lys Met Val Gln Gly Ser Gly Cys Phe Gly Arg Lys Met Asp
  1               5                  10                  15

Arg Ile Ser Ser Ser Ser Gly Leu Gly Cys Lys Gly Lys His Pro Leu
             20                  25                  30

Pro Pro Arg Pro Pro Ser Pro Ile Pro Val Ala Asp Thr Val Arg Val
         35                  40                  45

Thr Leu Gly Phe Val Val Ser Gly Asn His Thr Leu
     50                  55                  60

<210> SEQ ID NO 4
<211> LENGTH: 60
<212> TYPE: PRT
<213> ORGANISM: Artificial Sequence
<220> FEATURE:
<223> OTHER INFORMATION: synthetic polypeptide

<400> SEQUENCE: 4

Ser Pro Lys Met Val Gln Gly Ser Gly Cys Phe Gly Arg Lys Met Asp
  1               5                  10                  15

Arg Ile Ser Ser Ser Ser Gly Leu Gly Cys Lys Gly Lys His Pro Leu
             20                  25                  30

Pro Pro Arg Pro Pro Ser Pro Ile Pro Val Cys Asp Thr Val Arg Val
         35                  40                  45

Thr Leu Gly Phe Val Val Ser Gly Asn His Thr Leu
     50                  55                  60
```

NATRIURETIC PEPTIDE RECEPTOR-C AGONISTS

CROSS-REFERENCE TO RELATED APPLICATIONS

This application is a National Stage application under 35 U.S.C. §371 of International Application No. PCT/US2008/076434, having an International Filing Date of Sep. 15, 2008, which claims benefit of priority from U.S. Provisional Application Ser. No. 60/972,778, filed on Sep. 15, 2007.

BACKGROUND

1. Technical Field

This document relates to methods and materials involved in preferentially activating natriuretic peptide receptor-C polypeptides. For example, this document relates to agonists of natriuretic peptide receptor-C polypeptides as well as methods for activating natriuretic peptide receptor-C polypeptides.

2. Background Information

Members of the natriuretic polypeptide family are hormones that regulate body fluid homeostasis. Atrial natriuretic peptide (ANP) is secreted by atrial myocytes in response to increased intravascular volume. Once ANP is in the circulation, its effects are primarily on the kidney, vascular tissue, and adrenal gland, in which its actions lead to the excretion of sodium and water by the kidneys and a decrease in intravascular volume and blood pressure. BNP also is of myocardial cell origin, and like ANP, it circulates in human plasma. BNP is natriuretic, rennin inhibiting, vasodilating, and lusitropic. The main circulating and storage form of BNP is a 32 amino acid polypeptide with a ring structure. Physiological actions of BNP are mediated through a guanylate cyclase-linked receptor, natriuretic peptide receptor A (NPR-A). Clearance of BNP is promoted by a NPR-C receptor that removes it from the circulation. BNP also is degraded through enzymatic cleavage by neutral endopeptidase. C-type natriuretic peptide (CNP) is of endothelial cell origin and functions as a vasodilating and growth-inhibiting polypeptide. *Dendroaspis* natriuretic peptide (DNP) is similar in structure to ANP, BNP, and CNP, and is isolated from the venom of *Dendoaspis angusticeps* or green mamba snake.

SUMMARY

This document relates to methods and materials involved in preferentially activating natriuretic peptide receptor-C (NPR-C) polypeptides. For example, this document relates to agonists of NPR-C polypeptides as well as methods for activating NPR-C polypeptides. Agonists of NPR-C polypeptides can increase glomerular filtration rate without lowering blood pressure in a mammal. For example, agonists of NPR-C polypeptides can increase the removal of sodium from the body and can be used medically to treat hypertension, kidney disease, cirrhosis, congestive heart failure, or any sodium overload state.

In general, one aspect of this document features a method for activating an NPR-C polypeptide in a mammal. The method comprises identifying a mammal in need of an activated NPR-C polypeptide, and administering, to the mammal, an agonist of an NPR-C polypeptide. The NPR-C polypeptide can be a human NPR-C polypeptide. The mammal can be a human. The agonist can be ASBNP.1.

Another aspect of this document features a method for identifying an agent having an ability to increase diuretic or natriuretic activity within a mammal without substantially lowering blood pressure. The method comprises determining whether or not a test agent interacts with an NPR-C polypeptide to a greater extent than the test agent interacts with either an NPR-A polypeptide or an NPR-B polypeptide, wherein the presence of the greater interaction with the NPR-C polypeptide indicates that the test agent comprises the ability. The NPR-C polypeptide can be a human NPR-C polypeptide. The mammal can be a human.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document relates to methods and materials involved in preferentially activating natriuretic peptide receptor-C (NPR-C) polypeptides. For example, this document relates to agonists of NPR-C polypeptides as well as methods for activating NPR-C polypeptides. Agonists of NPR-C polypeptides can increase glomerular filtration rate without lowering blood pressure in a mammal. For example, agonists of NPR-C polypeptides can increase the removal of sodium from the body and can be used medically to treat hypertension, kidney disease, cirrhosis, congestive heart failure, or any sodium overload state.

An agonist of NPR-C polypeptides provided herein can be a polypeptide having the sequence set forth in SEQ ID NO:1, SEQ ID NO:2, SEQ ID NO:3 or SEQ ID NO:4. In some cases, an agonist of NPR-C polypeptides provided herein can contain an amino acid sequence that aligns to the sequence set forth in SEQ ID NO:1, SEQ ID NO:2, SEQ ID NO:3 or SEQ ID NO:4 with ten or less (e.g., nine or less, eight or less, seven or less, six or less, five or less, four or less, three or less, two or less, one, or zero) amino acid additions, deletions, substitutions, or combinations thereof. For example, an agonist of NPR-C polypeptides provided herein can contain the sequence set forth in SEQ ID NO:1 with the exception that first serine residue or the last valine residue of SEQ ID NO:1 is deleted or replaced with a different amino acid residue.

In some cases, an agonist of NPR-C polypeptides provided herein can contain (a) a first amino acid sequence that either is set forth in SEQ ID NO:1 or aligns to the sequence set forth in SEQ ID NO:1 with ten or less (e.g., nine or less, eight or less, seven or less, six or less, five or less, four or less, three or less, two or less, one, or zero) amino acid deletions, substitutions, or combinations thereof and (b) a second amino acid sequence that either is set forth in SEQ ID NO:2 or aligns to the sequence set forth in SEQ ID NO:2 with either (i) ten or less (e.g., nine or less, eight or less, seven or less, six or less, five or less, four or less, three or less, two or less, one, or zero) amino acid additions, substitutions, or combinations thereof provided that the addition or substitution does not result in the presence of a cysteine residue or (ii) 15 or less (e.g., 14 or less, 13 or less, twelve or less, eleven or less, ten or less, nine or less, eight or less, seven or less, six or less, five or less, four or less, three or less, two or less, one, or zero) amino acid deletions. For example, an agonist of NPR-C polypeptides provided herein can comprise or consist of the sequence set forth in SEQ ID NO:3 with the exception that the cysteine residue at position 43 of SEQ ID NO:3 is an amino acid other than cysteine (e.g., alanine, arginine, asparagines, aspartic acid, glutamine, glutamic acid, glycine, histidine, isoleucine, leucine, lysine, methionine, phenylalanine, praline, serine, threonine, tryptophan, tyrosine, or valine).

Polypeptides having one or more amino acid substitutions relative to a polypeptide sequence set forth in SEQ ID NO:1, SEQ ID NO:2, SEQ ID NO:3, or SEQ ID NO:4 can be prepared and modified as described herein. Amino acid substitutions can be conservative or non-conservative amino acid substitutions. Conservative amino acid substitutions include, for example, substitution of an acidic amino acid residue (e.g., aspartic acid or glutamic acid) with another acidic amino acid residue, substitution of a basic amino acid residue (e.g., lysine, arginine, or histidine) with another basic amino acid residue, substitution of a hydrophobic amino acid residue with another hydrophobic amino acid residue (e.g., substitution of leucine with isoleucine, methionine with valine, or alanine with valine), and substitution of a hydrophilic amino acid residue (e.g., serine, glycine, or threonine) with another hydrophilic amino acid residue.

Conservative amino acid substitutions also include substitution of an amino acid residue having a particular type of side chain with another amino acid residue having a similar type of side chain. For example, conservative amino acid substitutions include substitution of an amino acid residue having an aliphatic side chain (e.g., glycine, alanine, valine, leucine, or isoleucine) with another amino acid residue having an aliphatic side chain, substitution of an amino acid residue having an aliphatic-hydroxyl side chain (e.g., serine or threonine) with another amino acid residue having an aliphatic-hydroxyl side chain, substitution of an amino acid residue having an amide-containing side chain (e.g., asparagine or glutamine) with another amino acid residue having an amide-containing side chain, substitution of an amino acid residue having an aromatic side chain (e.g., phenylalanine, tyrosine, or tryptophan) with another amino acid residue having an aromatic side chain, substitution of an amino acid residue having a basic side chain (e.g., lysine, arginine, or histidine) with another amino acid residue having a basic side chain, and substitution of an amino acid residue having a sulfur-containing side chain (e.g., cysteine or methionine) with another amino acid residue having a sulfur-containing side chain.

An agonist of NPR-C polypeptides provided herein can be a polypeptide having any length. For example, an agonist of NPR-C polypeptides provided herein can be a polypeptide between 25 and 75 (e.g., between 30 and 70, between 32 and 60, between 32 and 57, between 32 and 50, between 32 and 45, between 35 and 43, or between 38 and 43) amino acid residues in length. It will be appreciated that an agonist of NPR-C polypeptides that is a polypeptide with a length of 25 or 75 amino acid residues is a polypeptide with a length between 25 and 75 amino acid residues.

In some cases, an agonist of NPR-C polypeptides provided herein can be between 37 and 47 amino acid residues in length and can comprise an amino acid sequence (a) set forth in SEQ ID NO:1 or (b) that aligns to the sequence set forth in SEQ ID NO:1 with five or less amino acid additions, deletions, substitutions, or combinations thereof. An example of such an agonist of NPR-C polypeptides includes, without limitation, an ASBNP.1 polypeptide. In some cases, an agonist of NPR-C polypeptides provided herein can be between 45 and 65 amino acid residues in length and can comprise (a) a first amino acid sequence that either is set forth in SEQ ID NO:1 or aligns to the sequence set forth in SEQ ID NO:1 with five or less amino acid deletions, substitutions, or combinations thereof and (b) a second amino acid sequence that either is set forth in SEQ ID NO:2 or aligns to the sequence set forth in SEQ ID NO:2 with (i) five or less amino acid additions, substitutions, or combinations thereof provided that the addition or substitution does not result in the presence of a cysteine residue or (ii) fifteen or less amino acid deletions. An example of such an agonist of NPR-C polypeptides includes, without limitation, an ASBNP.2 polypeptide.

In some cases, an agonist of NPR-C polypeptides provided herein can be a substantially pure polypeptide. As used herein, the term "substantially pure" with reference to a polypeptide means that the polypeptide is substantially free of other polypeptides, lipids, carbohydrates, and nucleic acid with which it is naturally associated. Thus, a substantially pure polypeptide is any polypeptide that is removed from its natural environment and is at least 60 percent pure or is any chemically synthesized polypeptide. A substantially pure polypeptide can be at least about 60, 65, 70, 75, 80, 85, 90, 95, or 99 percent pure. Typically, a substantially pure polypeptide will yield a single major band on a non-reducing polyacrylamide gel.

In some embodiments, an agonist of NPR-C polypeptides provide herein can lack the ability to stimulate production of cGMP in cells expressing human NPR-A or NPR-B polypeptides. Intracellular cGMP production can be assayed using, for example, the BIOTRACK cGMP enzyme immunoassay kit (Amersham Pharmacia Biotech). In other embodiments, an agonist of NPR-C polypeptides provide herein can lack vasoactivity. Vasoactivity can be assessed by determining responsitivity of a blood vessel (e.g., a carotid artery in an organ chamber) to the agonist.

In some cases, an agonist of NPR-C polypeptides can be a non-polypeptide compound. For example, an agonist of NPR-C polypeptides can be a small molecule or a peptide mimetic. An agonist of NPR-C polypeptides can have the ability to activate NPR-C polypeptides without exhibiting any agonistic activity at NPR-A or NPR-B polypeptides. In some cases, an agonist of NPR-C polypeptides can activate NPR-C polypeptides to a greater extent than the level of activity observed at NPR-A or NPR-B polypeptides. For example, an agonist of NPR-C polypeptides can be 10, 20, 30, 40, 50, 60, 70, 80, 90, or 100 percent more active at NPR-C polypeptides than at NPR-A or NPR-B polypeptides.

An agonist of NPR-C polypeptides provided herein can be formulated as a pharmaceutical composition by admixture with pharmaceutically acceptable non-toxic excipients or carriers. Such compositions can be administered to a subject in need thereof in an amount effective to treat, for example, heart, liver, kidney, or other sodium retaining conditions. For example, such compositions can be administered to a subject having a renal dysfunction. A renal dysfunction can include, without limitation, acute renal failure, glomerulonephritis, chronic renal failure, azotemia, uremia, immune renal disease; acute nephritic syndrome, rapidly progressive nephritic syndrome, nephrotic syndrome, Berger's Disease, chronic nephritic/proteinuric syndrome, tubulointerstital disease, nephrotoxic disorders, renal infarction, atheroembolic renal disease, renal cortical necrosis, malignant nephroangiosclerosis, renal vein thrombosis, renal tubular acidosis, renal glucosuria, nephrogenic diabetes insipidus, Bartter's Syndrome, Liddle's Syndrome, polycystic renal disease, interstitial nephritis, acute hemolytic uremic syndrome, medullary cystic disease, medullary sponge kidney, hereditary nephritis, and nail-patella syndrome.

Compositions provided herein also can be administered to a subject having a heart dysfunction. A heart dysfunction can include, without limitation, CHF, dilated congestive cardiomyopathy, hypertrophic cardiomyopathy, restrictive cardiomyopathy, mitral valve disease, aortic valve disease, tricuspid valve disease, angina pectoris, myocardial infarction, cardiac arrhythmia, pulmonary hypertension, arterial hypertension, renovascular hypertension, arteriosclerosis, atherosclerosis, and cardiac tumors.

Compositions provided herein also can be administered to a subject having an inflammatory condition. An inflammatory condition can include, without limitation, myocarditis, asthma, chronic inflammation, autoimmune diabetes, tumor angiogenesis, rheumatoid arthritis, rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis restenosis, cerebral malaria, chronic pulmonary inflammatory disease, silicosis, pulmonary sarcosis, bone resorption diseases such as osteoporosis, graft versus host reaction, Crohn's Disease, ulcerative colitis including inflammatory bowel disease (IBD), and pyresis.

Pharmaceutical compositions may be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Compositions for other routes of administration may be prepared as desired using standard methods.

Formulations for parenteral administration may contain as common excipients sterile water or saline, polyalkylene glycols such as polyethylene glycol, oils of vegetable origin, hydrogenated naphthalenes, and the like. In particular, biocompatible, biodegradable lactide polymer, lactide/glycolide copolymer, or polyoxethylene-polyoxypropylene copolymers are examples of excipients for controlling the release of an agonist of NPR-C polypeptides in vivo. Other suitable parenteral delivery systems include ethylene-vinyl acetate copolymer particles, osmotic pumps, implantable infusion systems, and liposomes. Formulations for inhalation administration may contain excipients such as lactose, if desired. Inhalation formulations may be aqueous solutions containing, for example, polyoxyethylene-9-lauryl ether, glycocholate and deoxycholate, or they may be oily solutions for administration in the form of nasal drops. If desired, the compounds can be formulated as gels to be applied intranasally. Formulations for parenteral administration may also include glycocholate for buccal administration.

For oral administration, tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Nasal preparations can be presented in a liquid form or as a dry product. Nebulised aqueous suspensions or solutions can include carriers or excipients to adjust pH and/or tonicity.

An agonist of NPR-C polypeptides described herein also can be formulated for topical delivery. Topical application and/or delivery of an agonist of NPR-C polypeptides provided herein can be achieved using known methods, e.g., iontophoresis or lipogels.

Compositions described herein (e.g., including an agonist of NPR-C polypeptides provided herein) can additionally include other active ingredients.

Various clinical parameters can be monitored prior to, during, and/or after administering an agonist of NPR-C polypeptides described herein (e.g., formulated as a pharmaceutical composition) to a subject (e.g., a subject having a renal or heart dysfunction or an inflammatory condition). For example, vital signs, electrolytes, serum creatinine, cystatin, urinary BNP levels, plasma BNP levels, urine output, plasma levels of the administered agonist of NPR-C polypeptides, urine levels of the administered agonist of NPR-C polypeptides, or any combination thereof can be monitored. In some cases, plasma renin activity, glomerular filtration rate, urinary cGMP excretion, plasma cGMP levels, urinary ANP excretion, urinary BNP excretion, cardiac output, systemic vascular resistance, aldosterone levels, or any combination thereof can be monitored. Any appropriate method can be used to monitor clinical parameters including, without limitation, the methods described herein.

Monitoring clinical parameters can allow a clinician to determine whether or not an administered agonist is effective, e.g., whether or not the severity of a symptom of a heart or renal dysfunction or inflammatory condition has been reduced. In addition, monitoring clinical parameters before, during, and/or after administration of an agonist provided herein can indicate whether the dose of the agonist should be increased or decreased, whether administration of the agonist should be continued or discontinued, or whether the agonist should be re-administered. Monitoring clinical parameters also can indicate the severity of a subject's condition, which, in turn, can provide guidance as to when an agonist provided herein should be administered and at what dose.

This document also provides methods and materials for identifying an agonist of NPR-C polypeptides. For example, test agents can be screened for the ability to interact with NPR-C polypeptides using cell based activity assays or receptor binding assays as described herein. In some cases, test agents can be screened for the ability to preferentially interact with NPR-C polypeptides as compared to NPR-A polypeptides or NPR-B polypeptides. For example, an agonist of NPR-C polypeptides lacking the ability to activate NPR-A polypeptides and NPR-B polypeptides can be identified using the cell based activity assays or receptor binding assays as described herein.

The invention will be further described in the following examples, which do not limit the scope of the invention described in the claims.

EXAMPLES

Example 1

Natriuretic Peptide Receptor Activities

HEK293 cells stably expressing rat NPR-A or NPR-B were prepared using methods similar to those described elsewhere (Fan et al., *Mol. Pharmacol.*, 67:174-83 (2005); and Bryan and Potter, *J. Biol. Chem.*, 277:16041-16047 (2002)). The cells were maintained in Dulbecco's modified Eagle's medium (DMEM) supplemented with 10% FBS, 100 units/mL penicillin, 100 μg/mL streptomycin, and 200 μg/mL G418. The cells were plated in 48-well plates and grown to 90% confluency. On the day of the assay, the cells were incubated in serum-free medium for 4 hours. The cells were pretreated for 10 minutes at 37° C. in DMEM containing 25 mM HEPES, pH 7.4 and 0.5 mM 1-methyl-3-isobutylxanthine by aspirating the starvation medium. After pretreatment, the medium was replaced with the same medium containing the indicated concentrations of natriuretic peptides. The cells were stimulated for 3 minutes with CNP, rat BNP, human BNP, ASBNP, or ASBNP.1. The reaction was stopped by aspiration of the medium and addition of 200 μL ice-cold 80% ethanol. Cyclic GMP concentrations were estimated from an aliquot of the ethanol extract using a Perkin Elmer cGMP RIA kit without acetylation as described elsewhere (Bryan and Potter, *J. Biol. Chem.*, 277:16041-16047 (2002); and Abbey and Potter, *J. Biol. Chem.*, 277:42423-30 (2002)).

Figure 1:
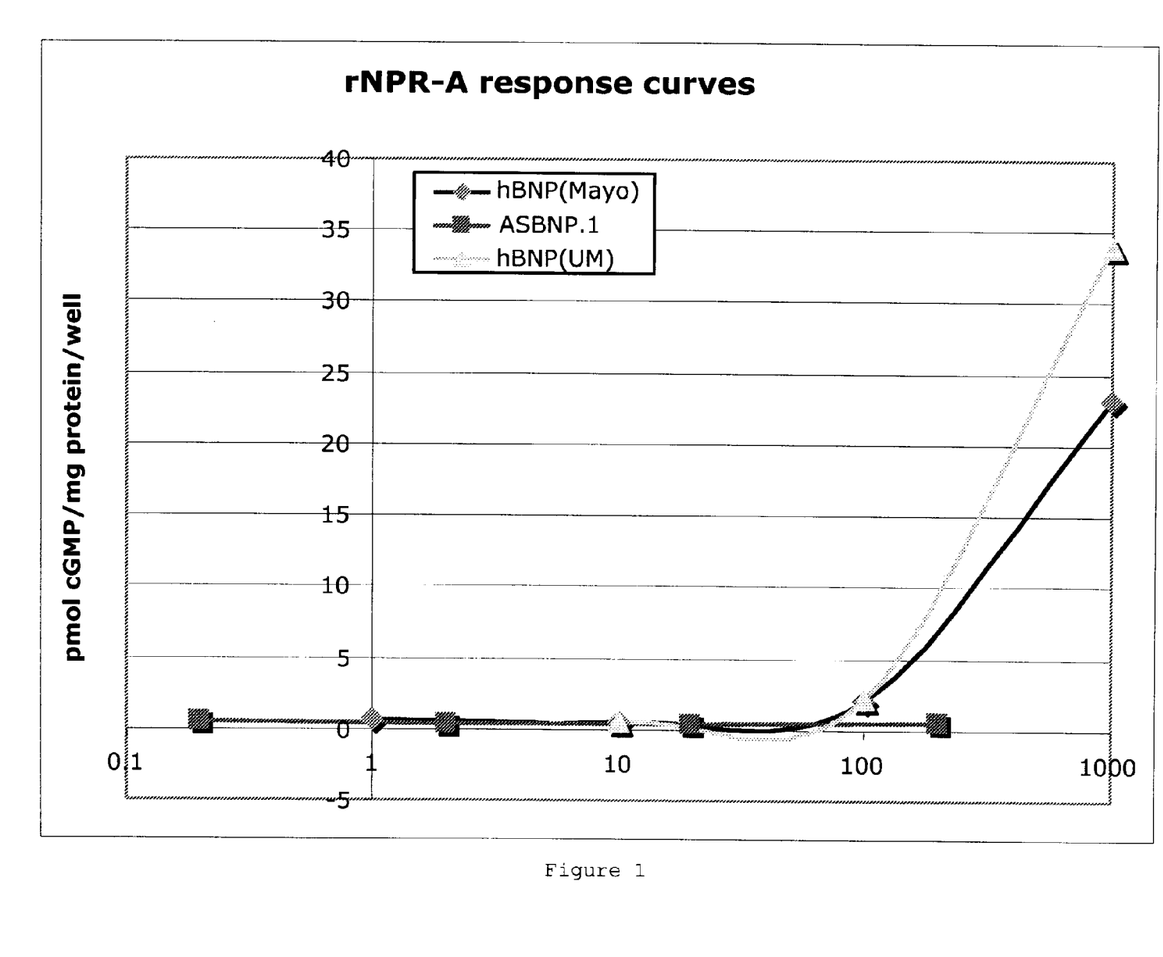
FIG. 1 is a graph plotting pmol cGMP/mg protein/well for HEK293 cells stably expressing rat NPR-A and treated with the indicated amount (μM) of human BNP from a first source, ASBNP.1 (also referred to as BNP2.1), or human BNP from a second source.
Figure 2:
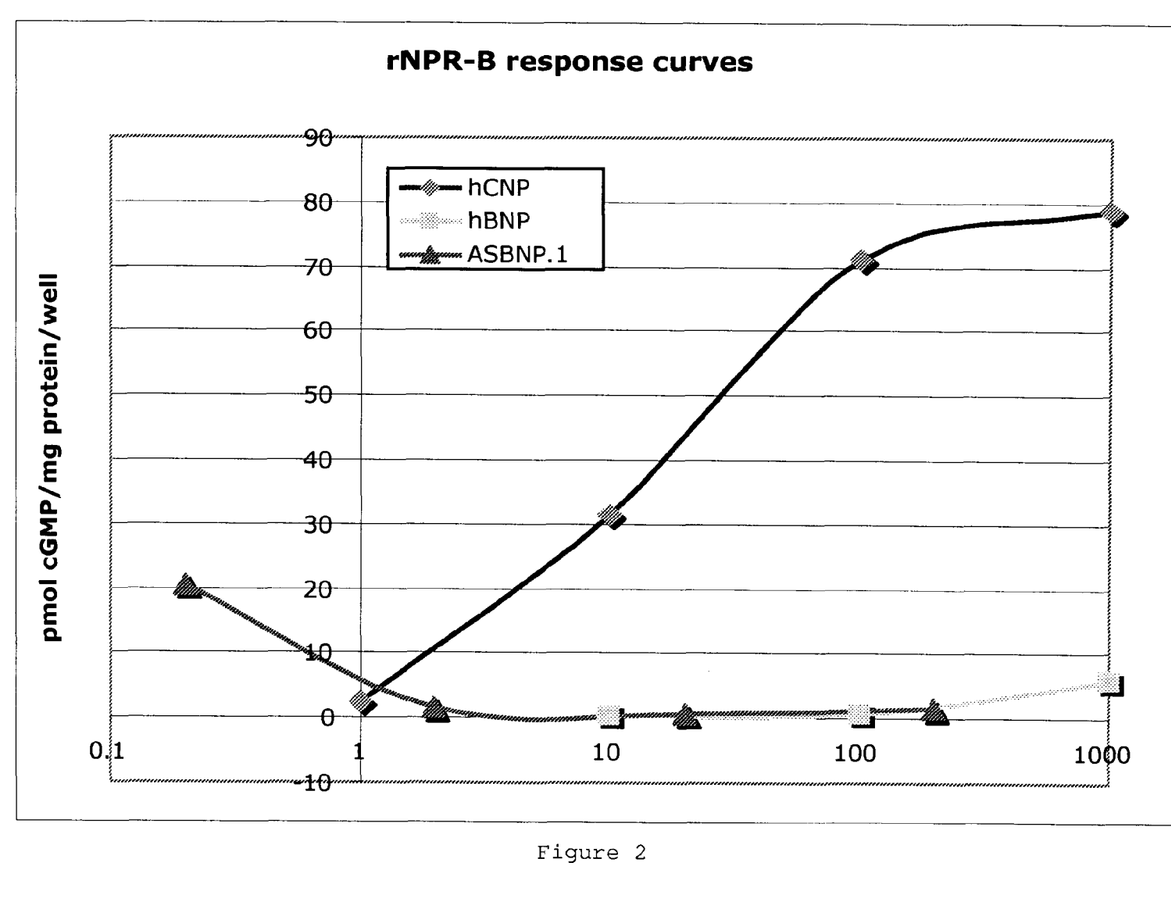
FIG. 2 is a graph plotting pmol cGMP/mg protein/well for HEK293 cells stably expressing rat NPR-B and treated with the indicated amount (μM) of a human CNP, human BNP, or ASBNP.1 polypeptide.
Figure 5:
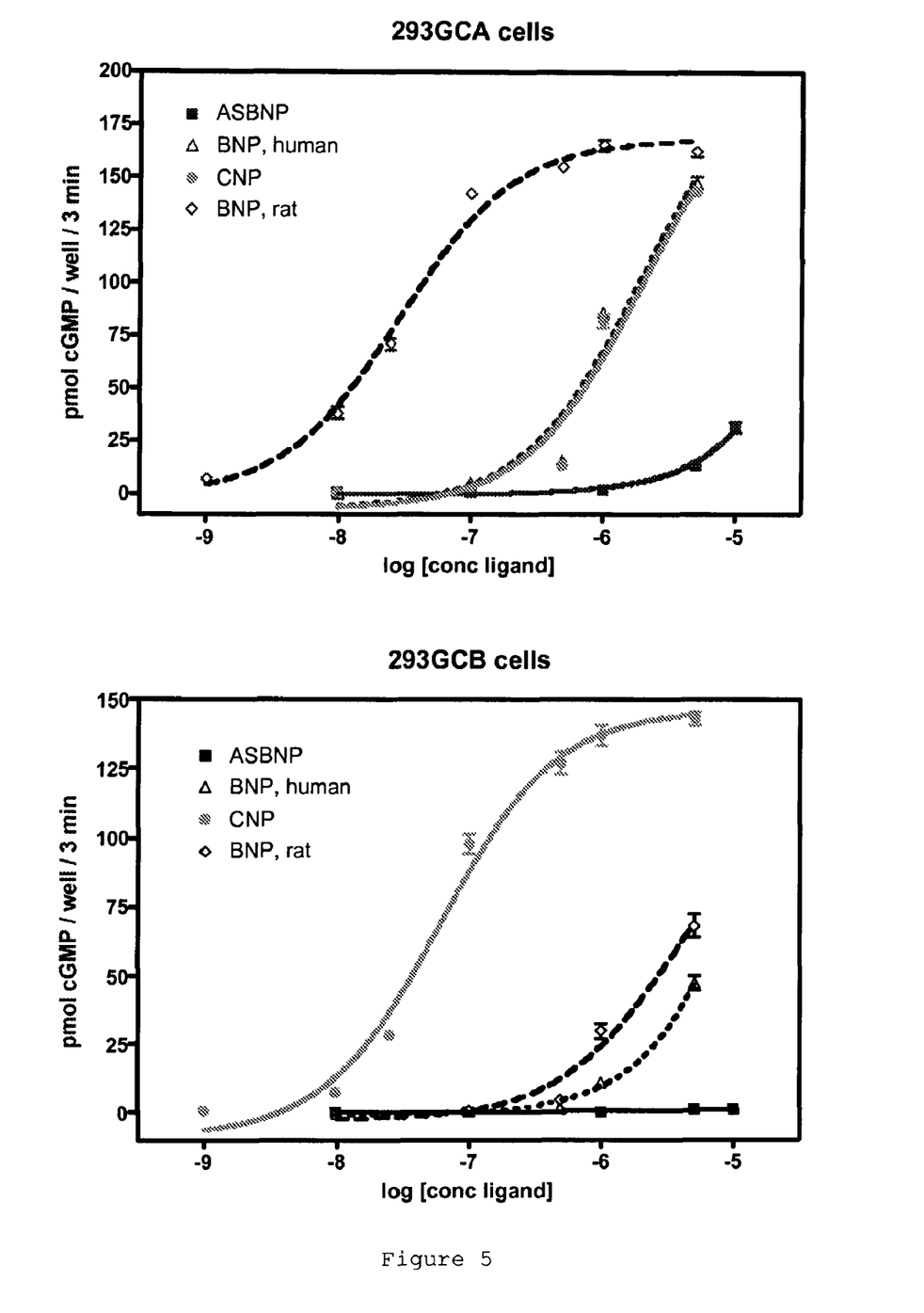
FIG. 5 is a graph plotting pmol cGMP/well/3 minutes for HEK293 cells stably expressing rat NPR-A (top; 293GCA cells) or rat NPR-B (bottom; 293GCB cells) and treated with increasing amounts of the indicated polypeptides.

BNP activated cells expressing rat NPR-A at concentrations in the mM range, whereas ASBNP.1 did not exhibit any activity for cells expressing rat NPR-A (FIG. 1). CNP activated cells expressing rat NPR-B, whereas BNP and ASBNP.2 exhibited little, if any, activity on cells expressing rat NPR-B (FIG. 2). Concentration curves were determined for CNP, rat BNP, human BNP, and ASBNP using HEK293 cells stably expressing rat NPR-A (293GCA cells) or NPR-B (293GCB cells) (FIG. 5).

Figure 3:
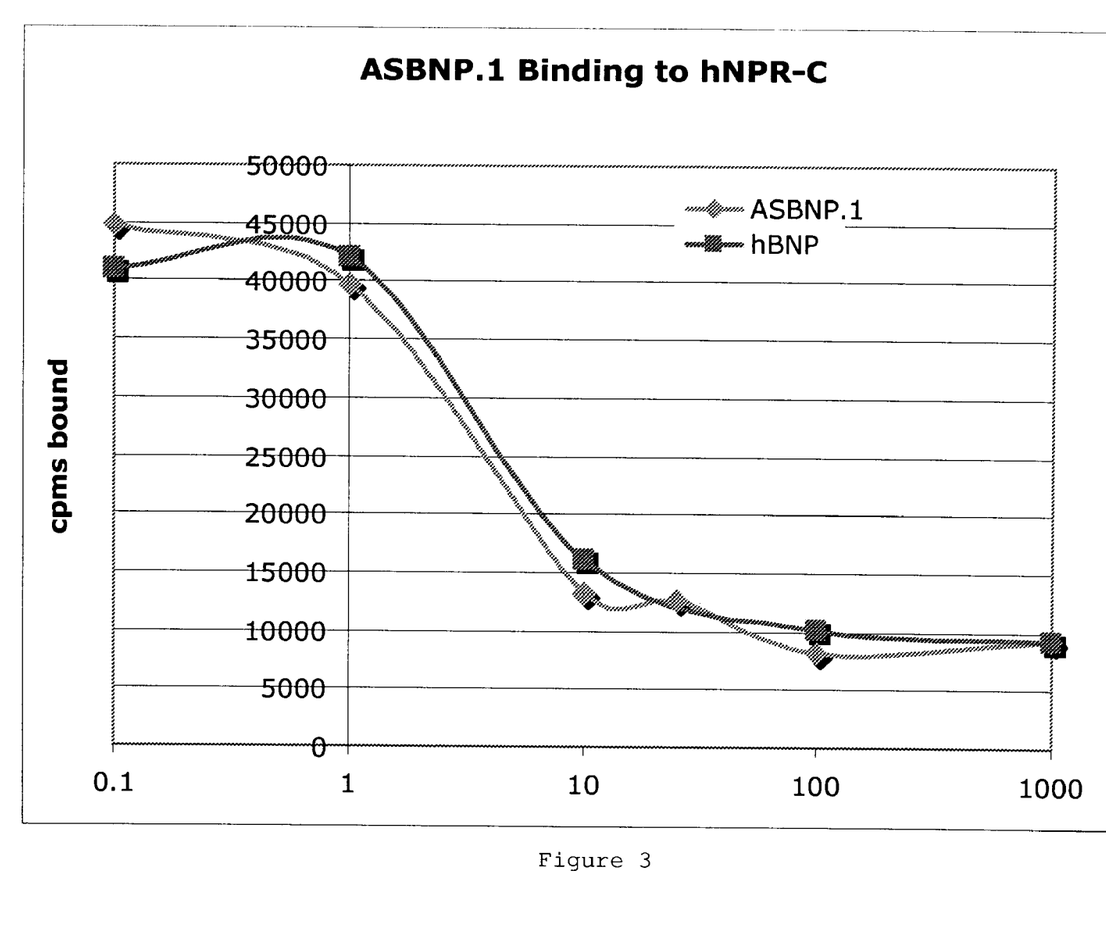
FIG. 3 is a graph plotting the amount of binding to human NPR-C.
Figure 4:
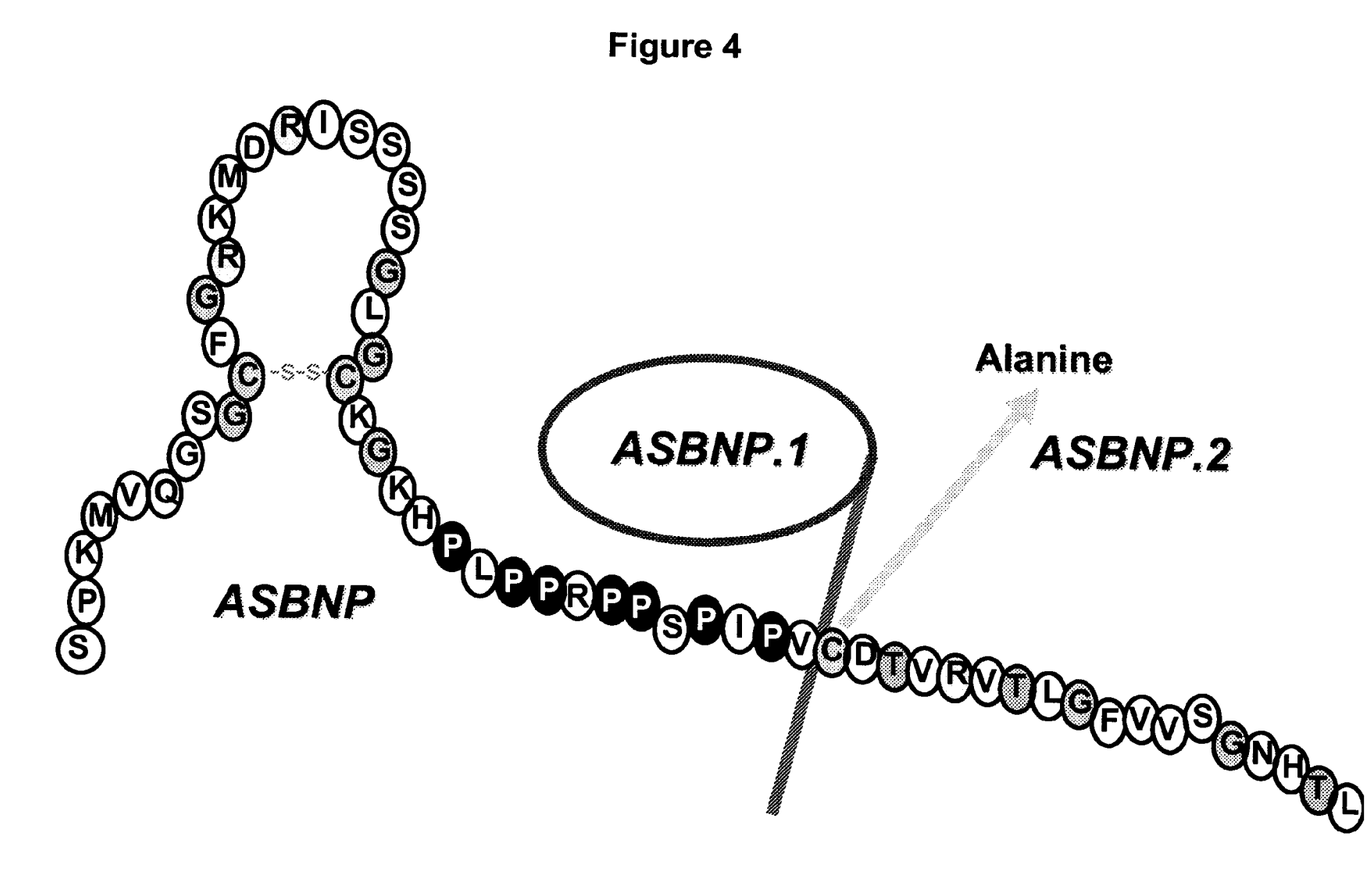
FIG. 4 is a schematic diagram of an ASBNP polypeptide that is 60 amino acid residues in length (SEQ ID NO:4), an ASBNP.1 polypeptide that is 42 amino acid residues in length (SEQ ID NO:1), an ASBNP.2 polypeptide that is 60 amino acid residues in length with an alanine at position 43 (SEQ ID NO:3). The sequence of ASBNP.2 from the alanine at position 43 to the leucine at position 60 is 18 amino acid residues in length (SEQ ID NO:2). ASBNP (also referred to as BNP2) is a variant form of BNP generated by alternative splicing.

Human BNP and ASBNP.1 binding to human NPR-C was assessed using methods similar to those described elsewhere (Fan et al., *Mol. Pharmacol.*, 67:174-83 (2005)). Both BNP and ASBNP.1 exhibited binding to human NPR-C (FIG. 3).

These results demonstrate that ASBNP.1 can activate NPR-C polypeptides and can induce its biological effects preferentially via NPR-C polypeptides and not NPR-A polypeptides or NPR-B polypeptides.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for activating an NPR-C polypeptide in a mammal, wherein said method comprises:
   (a) identifying a mammal in need of an increased glomerular filtration rate without lowering blood pressure, and
   (b) administering, to said mammal, an amount of an agonist of an NPR-C polypeptide effective to activate an NRP-C polypeptide in said mammal, thereby increasing glomerular filtration rate in said mammal without lowering blood pressure, wherein said agonist is ASBNP.1.

2. The method of claim 1, wherein said mammal is a human.

* * * * *

UNITED STATES PATENT AND TRADEMARK OFFICE
CERTIFICATE OF CORRECTION

PATENT NO. : 8,357,656 B2
APPLICATION NO. : 12/677838
DATED : January 22, 2013
INVENTOR(S) : Simari et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 247 days.

Signed and Sealed this
First Day of September, 2015

Michelle K. Lee
*Director of the United States Patent and Trademark Office*